(12) United States Patent
Yoshii et al.

(10) Patent No.: US 8,021,044 B2
(45) Date of Patent: Sep. 20, 2011

(54) X-RAY TOMOGRAPHY APPARATUS

(75) Inventors: Yasuo Yoshii, Kawasaki (JP); Harunobu Fukushima, Tokyo (JP); Hitoshi Hattori, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 41 days.

(21) Appl. No.: 12/493,557

(22) Filed: Jun. 29, 2009

(65) Prior Publication Data

US 2009/0323890 A1    Dec. 31, 2009

(30) Foreign Application Priority Data

Jun. 30, 2008   (JP) .................................. 2008-171201

(51) Int. Cl.
*H05G 1/06*   (2006.01)
*H05G 1/02*   (2006.01)

(52) U.S. Cl. .......................................... 378/197; 378/15

(58) Field of Classification Search ................ 378/4–20, 378/193, 197, 203, 204, 210
See application file for complete search history.

(56) References Cited

U.S. PATENT DOCUMENTS 4,199,154 A * 4/1980 Mueller ........................ 277/420
5,761,269 A * 6/1998 Sugihara et al. ............. 378/199

FOREIGN PATENT DOCUMENTS

JP          6005340 A    1/1994
JP     2003-260048 A    9/2003

* cited by examiner

*Primary Examiner* — Anastasia Midkiff
(74) *Attorney, Agent, or Firm* — Ohlandt, Greeley, Ruggiero & Perle, L.L.P.

(57) ABSTRACT

Fins are arranged on the rotating side of an X-ray computed tomography apparatus. The fins are rotated to generate airflow as the rotating side is rotated. This airflow serves to discharge wear debris to the outside of the X-ray CT apparatus, thereby preventing the wear debris from scattering toward an X-ray tube and support bearing. In consequence, in the X-ray CT apparatus provided with a slip ring, the wear debris produced in a contact space between the slip ring and a brush can be prevented from being scattered in the apparatus.

7 Claims, 5 Drawing Sheets

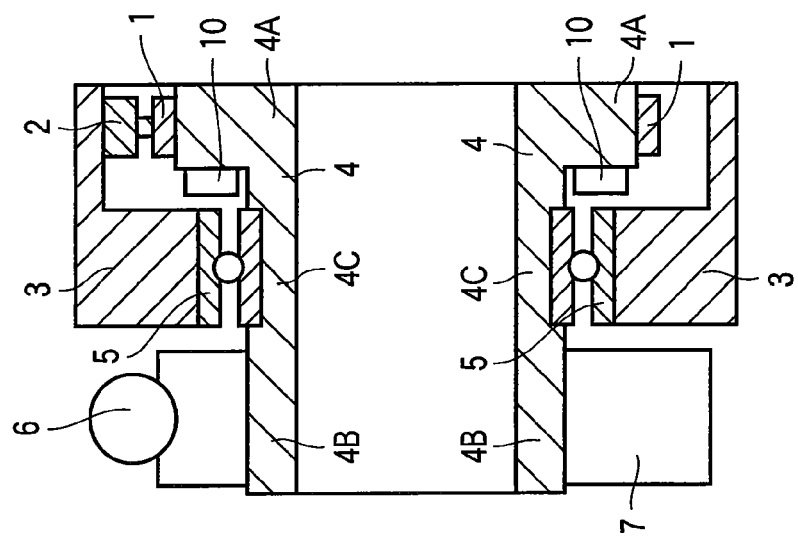
F I G. 1B
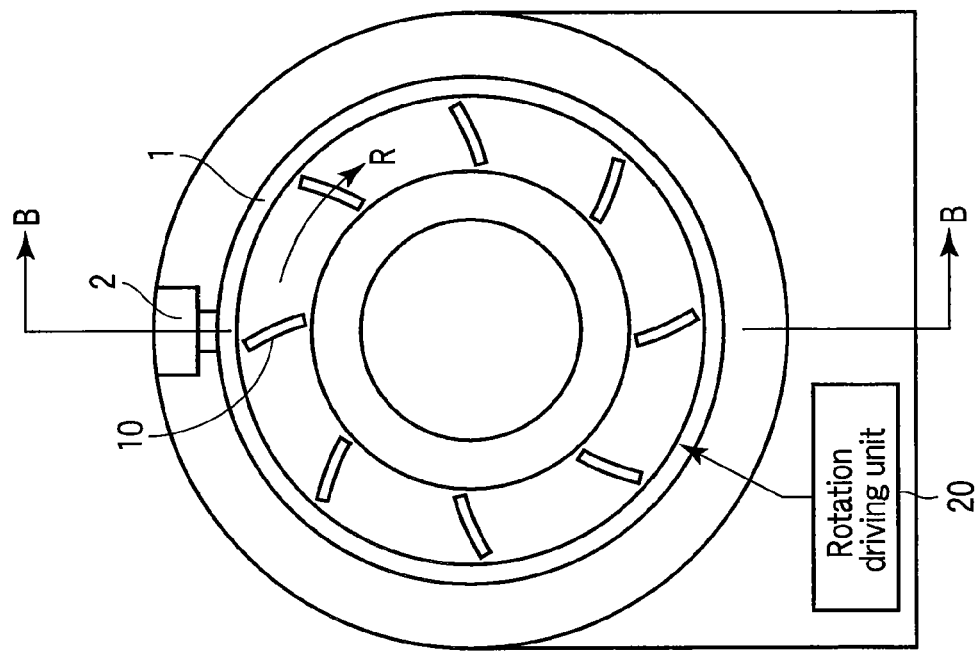
F I G. 1A

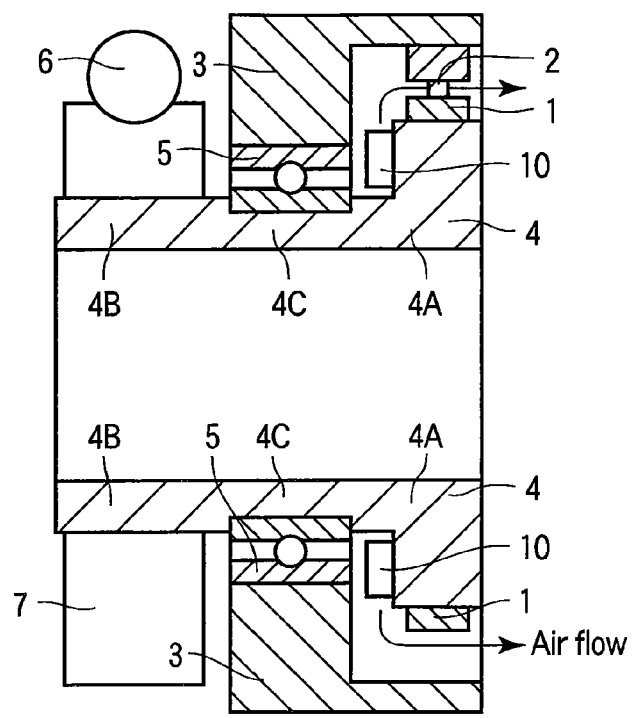
F I G. 2
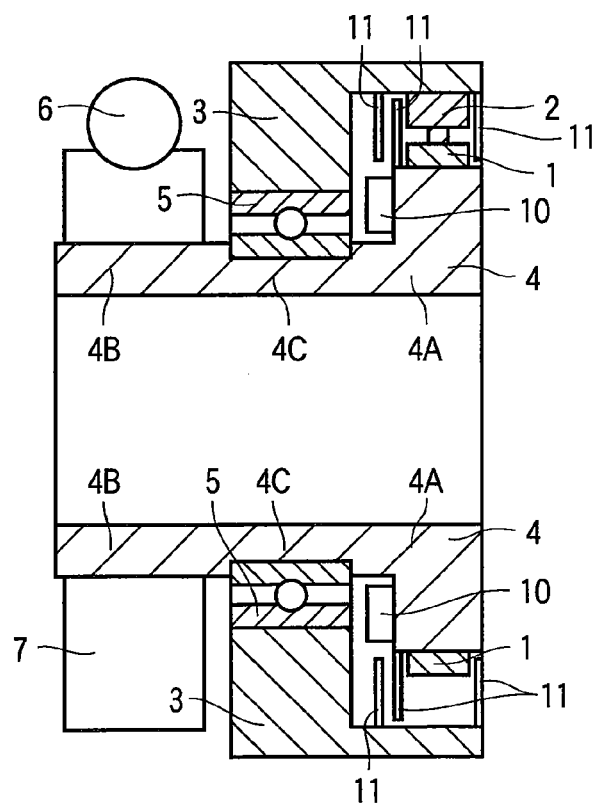
F I G. 3

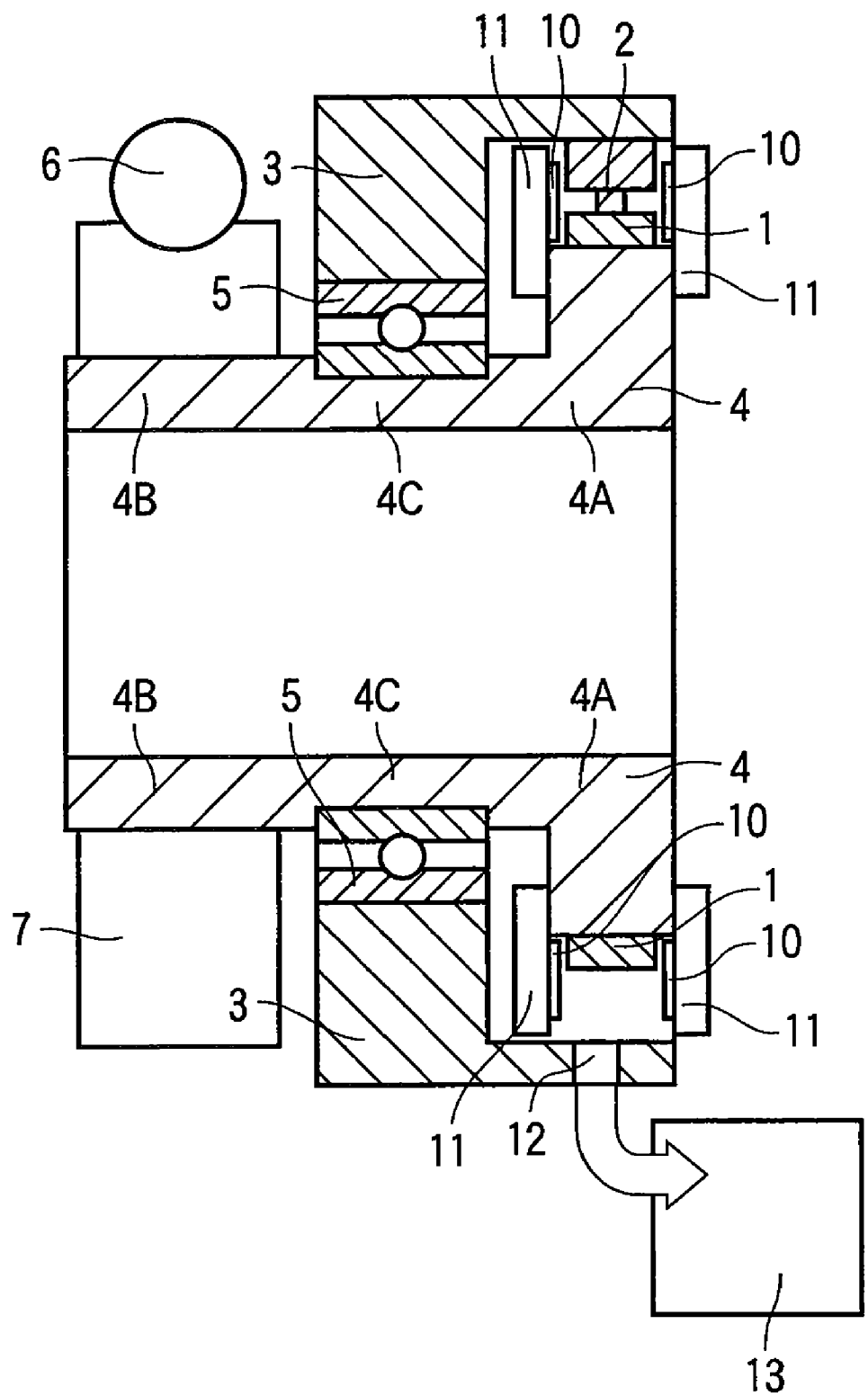
F I G. 5

X-RAY TOMOGRAPHY APPARATUS

CROSS-REFERENCE TO RELATED APPLICATIONS

This application is based upon and claims the benefit of priority from prior Japanese Patent Application No. 2008-171201, filed Jun. 30, 2008, the entire contents of which are incorporated herein by reference.

BACKGROUND OF THE INVENTION

1. Field of the Invention

The present invention relates to an X-ray tomography apparatus with a slip ring.

2. Description of the Related Art

In an X-ray computed tomography (CT) apparatus of the continuous-rotation type, an X-ray tube and X-ray detector are arranged opposite each other on a rotating frame, whereby the rotating frame is rotated. Electrical power supply and/or electrical signal transfer is needed between the rotating and stationary sides of the rotating frame. Normally, this electrical power supply and/or electrical signal transfer is performed through a slip ring which is attached to the rotating frame on the rotating side and a brush on the stationary side. The slip ring is rotated as the rotating frame is rotated, and is continuously brought into contact with the brush fixed on the stationary side. Therefore, wear debris is generated from friction portions of the slip ring and brush. If the wear debris scatters in the X-ray CT apparatus, it may adversely affect electronic components and the like mounted in the apparatus. If the wear debris enters a support bearing that supports the rotating frame, for example, it causes mechanical wear and shortens the life of the bearing. If the wear debris adheres to circuits of precision electronic devices, such as the X-ray tube, X-ray detector, etc., it may break electrical insulation and cause malfunctioning of the devices.

In this background, JP-A H06-5340 (KOKAI) discloses an X-ray CT apparatus in which wear debris is prevented from scattering anywhere from a slip ring by a labyrinth seal or dust seal that is installed near the slip ring.

However, recent X-ray CT apparatuses are improved so that a rotating frame with an X-ray tube and X-ray detector is rotated at high speed to obtain higher-definition images. Since the slip ring, as well as the rotating frame, is rotated at high speed, friction speeds of the slip ring and brush increase, so that the production of wear debris tends to increase. In an X-ray CT apparatus furnished with a non-contact seal, such as a labyrinth seal or shield plate, there is a gap between a rotating frame and stationary-side frame such that the wear debris leaks through it. Therefore, the wear debris cannot be prevented from scattering in the apparatus.

Thus, according to the conventional X-ray CT apparatus with the slip ring, the labyrinth seal cannot fully prevent scattering of wear debris, so that it is difficult to prevent the wear debris from scattering in the apparatus in which the electronic devices and the like are installed. In consequence, the X-ray CT apparatus preferably securely prevent wear debris from scattering in it.

BRIEF SUMMARY OF THE INVENTION

According to an aspect of the invention, there is provided an X-ray computed tomography apparatus comprising:

an X-ray source which irradiates a subject with X-rays;

an X-ray detection unit which detects the X-rays transmitted through the subject and produces a detection signal;

a rotating frame which supports the X-ray source and the X-ray detection unit so as to be opposed to each other with the subject and is rotated around the subject;

a bearing which rotatably supports the rotating frame;

a support frame which supports the bearing;

an electrically conductive brush disposed on the support frame;

a slip ring which is annularly disposed on the rotating frame in a direction of rotation of the rotating frame, mechanically contacts the brush, and is configured to supply an electrical power to the rotating frame, wear debris being produced in a contact area between the slip ring and the brush; and a plurality of fins arranged on the rotating frame and are rotated with the rotating frame to produce airflow flowing from a side of the bearing to the outside of the apparatus in such a manner that the airflow transports the wear debris to the outside of the apparatus.

According to another aspect of the invention, there is provided a n X-ray computed tomography apparatus comprising:

an X-ray source which irradiates a subject with X-rays;

an X-ray detection unit which detects the X-rays transmitted through the subject and produces a detection signal;

a rotating frame which supports the X-ray source and the X-ray detection unit so as to be opposed to each other with the subject and is rotated around the subject;

a bearing which supports the rotating frame for rotation;

a support frame which supports the bearing;

an electrically conductive brush disposed on the support frame;

a slip ring which is annularly disposed on the rotating frame in a direction of rotation of the rotating frame, mechanically contacts the brush, and is configured to supply an electrical power to the rotating frame, wear debris being produced in a contact area between the slip ring and the brush;

a plurality of fins arranged on the rotating frame and are rotated with the rotating frame to produce airflow flowing from a side of the bearing to the contact space;

an exhaust port which communicates with the contact space through which the airflow is guided and transports the wear debris; and a dust collection unit which is coupled to the exhaust port and serves to collect the wear debris transported through the exhaust port.

BRIEF DESCRIPTION OF THE SEVERAL VIEWS OF THE DRAWING

FIG. 1A is a front view schematically showing an X-ray CT apparatus according to an embodiment of the invention;

FIG. 1B is a schematic sectional view of the X-ray CT apparatus shown in FIG. 1A;

FIG. 2 is a schematic view showing how an airflow is generated by fins shown in FIG. 1B;

FIG. 3 is a sectional view schematically showing an X-ray CT apparatus according to another embodiment of the invention provided with a labyrinth seal;

FIG. 5 is a sectional view showing an X-ray CT apparatus according to a further embodiment of the invention.

DETAILED DESCRIPTION OF THE INVENTION

Figure 4:
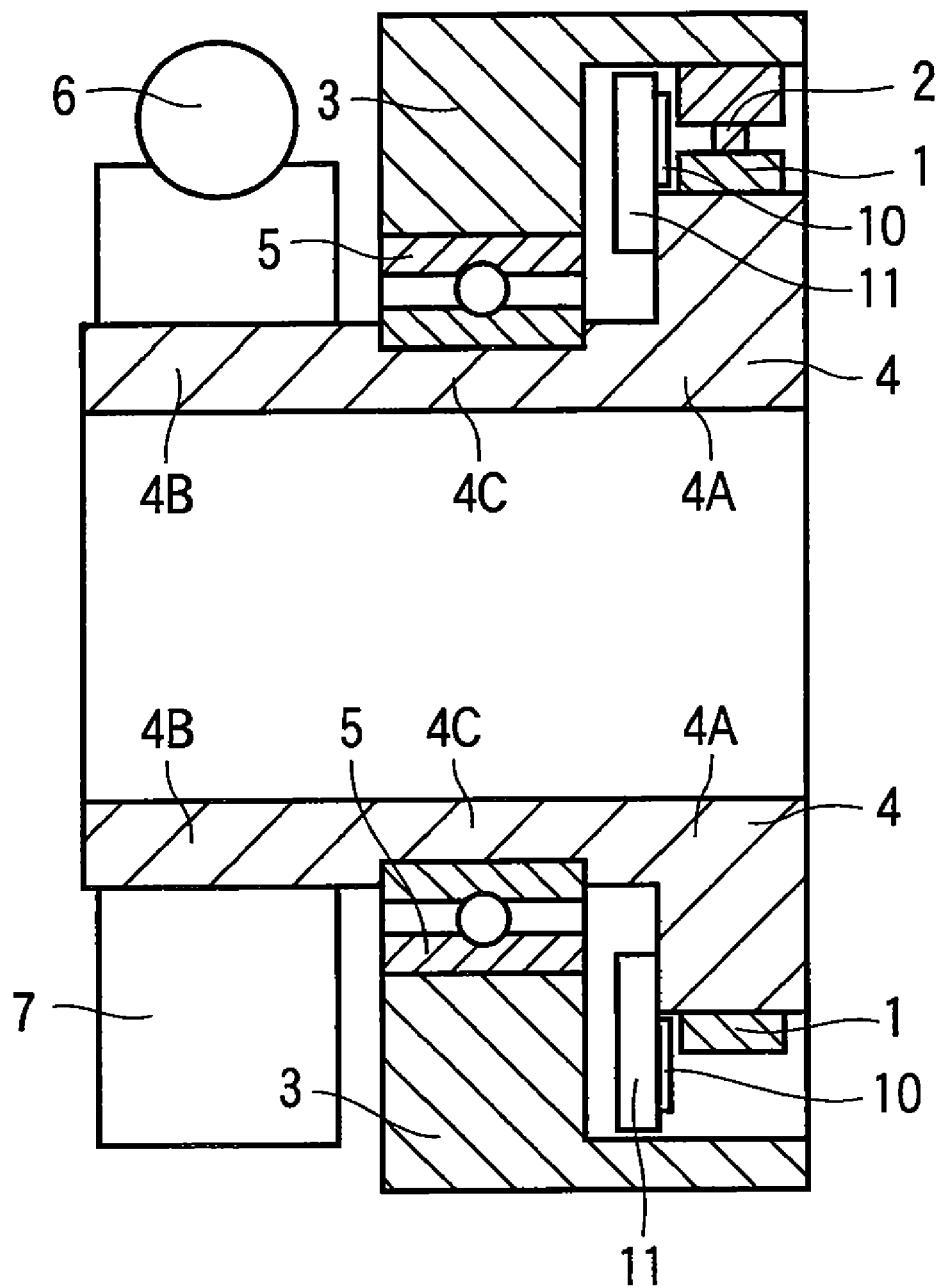
FIG. 4 is a sectional view showing an X-ray CT apparatus according to still another embodiment of the invention.

X-ray CT apparatuses according to the embodiments of the present invention will now be described with reference to the accompanying drawings.

FIG. 1A is a front view schematically showing an X-ray CT apparatus according to an embodiment of the invention. FIG. 1B is a sectional view taken along line B-B of FIG. 1A. The X-ray CT apparatus is provided with an X-ray tube 6 for irradiating a subject with X-rays and an X-ray detector 7 for detecting the X-rays transmitted through the subject. The X-ray tube 6 and X-ray detector 7 are arranged on a rotating frame 4 of the rotating side so as to face each other with the central axis of the rotating frame 4. The rotating frame 4 is rotatably supported on a support bearing 5 which are provide around the rotating frame 4 and are attached to a support frame 3 on the stationary side. Further, the rotating frame 4 is provided with a hollow portion that accommodates a stage (not shown) on which the subject is to be placed. The rotating frame 4 is driven by a rotation driving unit 20 to rotate continuously in a rotation direction R. Thus, an X-ray beam from the X-ray tube 6 is generated in a fan-like shape and applied to the subject. The X-ray beam passing through the subject is detected by the X-ray detector 7. The subject is exposed to the X-ray beam throughout it circumference. The X-rays transmitted through the subject in various directions within one plane are detected by the X-ray detector 7 and converted into an X-ray detection signal. The detection signal is processed by an external processing circuit to reconstruct an X-ray transmission image so that a tomography image of a region of interest (ROI) can be visually displayed.

Further, the rotating frame 4 is provided with a slip ring 1, through which an electrical power is supplied from the support frame 3 on the stationary side to the rotating frame 4 on the rotating side. The slip ring 1 is fixed to the rotating frame 4 so as to extend annularly in the rotation direction R of the rotating frame 4. As the rotating frame 4 is rotated, the slip ring 1 is rotated and continuously brought into mechanical and electrical contact with an electrically conductive brush 2, which is installed on the support frame 3 on the stationary side. The brush 2 is connected to an external power source. The slip ring 1 and brush 2 are in contact with each other when the electrical power is supplied from the stationary side to rotating side.

A signal may be transferred between the rotating frame 4 on the rotating side and the support frame 3 on the stationary side through the slip ring 1 and brush 2. The detection signal detected by the X-ray detector 7 is transferred from the rotating side to stationary side through the slip ring 1 and brush 2 and delivered to a signal processor, which is connected to the brush 2. The signal may be transferred in a non-contact manner instead of being transferred through the slip ring 1 and brush 2. In this case, the rotating and stationary sides are optically coupled by an optical fiber in order to transfer the detection signal from the rotating side to stationary side. In the apparatus constructed in this manner, only the electrical power from the stationary side to rotating side is supplied through the slip ring 1 and brush 2.

Since the slip ring 1 and brush 2 are in contact with each other when the ring 1 is rotated, the ring 1 or brush 2 wears and produces wear debris. In order to discharge the wear debris to the outside, the rotating frame 4 is provided with fins 10 arranged along the slip ring 1. The fins 10 are rotated to generate airflow as the rotating frame 4 is rotated. The wear debris is compulsorily discharged to the outside of the X-ray CT apparatus by this airflow. In consequence, the wear debris can be prevented from inhibiting electrical contact or signal transmission between the slip ring 1 and brush 2 or from scattering toward electrical components or circuits.

The following is a detailed description of the arrangement relationship between the X-ray tube 6 and slip ring 1. As shown in FIG. 1A, the rotating frame 4 is substantially in the form of a cylinder that is open on either side and extends along an axis of rotation. The X-ray tube 6 and X-ray detector 7 are opposed to a cylindrical portion 4B on one opening side of the cylindrical rotating frame 4 with the hollow portion for the subject. On the other opening side of the rotating frame 4, moreover, the slip ring 1 extends annularly around a large-diameter circumferential portion 4A. The support bearing 5 including a bearing element is disposed around a substantially central portion 4C of the rotating frame 4 between the slip ring 1 and X-ray tube 6, and it is rotatably supported on the support frame 3 by the support bearing 5.

The circumferential portion 4A is larger in diameter than the central portion 4C and cylindrical portion 4B and has an annular inner surface on the side of the support bearing 5. The fins 10 are fixed to the inner surface. The fins 10 are arranged so that air is caused to flow from the support bearing 5 toward the slip ring 1 as they rotate. As mentioned before, therefore, wear debris produced on the slip ring 1 is discharged outward from the apparatus by the airflow. Thus, the fins 10 are rotated as the rotating frame 4 is rotated in the rotation direction R, whereupon an airflow directed from the fins 10 to the slip ring 1 is generated. As shown in FIG. 3, this airflow is directed to the slip ring 1 and is forced out of the X-ray CT apparatus through a space between the slip ring 1 and support frame 3.

When the rotating frame 4 rotates in the X-ray CT apparatus constructed in this manner, the slip ring 1 rotates in contact with the brush 2, so that wear debris is generated from a contact portion. At the same time, the fins 10 attached to the rotating frame 4 are rotated, whereupon airflow is generated. The wear debris is discharged to the outside of the X-ray CT apparatus by this airflow. Thus, the wear debris can be prevented from leaking out or scattering toward the support bearing 5, X-ray tube 6, X-ray detector 7, which are situated on the upstream side of the slip ring 1 with respect to the airflow, as viewed from the location of the fins 10.

The following is a description of an X-ray CT apparatus according to another embodiment.

In the X-ray CT apparatus according to the embodiment shown in FIG. 3, a labyrinth seal 11 is disposed near a slip ring 1. The seal 11 is a non-contact seal configured to prevent scattering of wear debris, and it is composed of a pair of seal rings. One of the seal rings is fixed on a large-diameter circumferential portion 4A of a rotating frame 4 so as to extend along the annular slip ring 1. The other seal ring of the labyrinth seal 11 is fixed to a support frame 3 on the stationary side so as to face the one seal ring with a small gap. Since the labyrinth seal 11 is located between the slip ring 1 and a support bearing 5, wear debris generated from the slip ring 1 can be prevented from scattering toward the support bearing 5. Since the labyrinth seal 11 has the small gap, an airflow generated by the fins 10 as the rotating frame 4 rotates can be discharged to the outside of the X-ray CT apparatus through the gap and a space over the slip ring 1. Thus, the wear debris can be discharged from the apparatus by the airflow generated by the fins 10.

The labyrinth seal 11 may be configured to be a simple cover plate if it can prevent scattering of wear debris.

In the X-ray CT apparatus according to this embodiment, the wear debris can be prevented from scattering toward the support bearing 5 not only by the airflow generated by the fins 10 but also by the labyrinth seal 11. Thus, the wear debris can be securely prevented from scattering in the X-ray CT apparatus.

In an X-ray CT apparatus according to an embodiment shown in FIG. 4, moreover, a labyrinth seal 11 is composed of a seal ring fixed to the inner peripheral surface of a large-diameter circumferential portion 4A, and a small gap is formed between a circumferential end face of the seal ring and the inner peripheral surface of a support frame 3. Since the labyrinth seal 11 is disposed so as to close the space between the circumferential portion 4A and the inner peripheral surface of the support frame 3, a slip ring 1 and support bearing 5 are spatially divided by the labyrinth seal 11. Further, fins 10 are fixedly installed on a side surface of the labyrinth seal 11 nearer to the slip ring 1 so that an airflow generated by the fins 10 can be discharged through the support bearing 5 toward the slip ring 1. Also in this embodiment, wear debris can be prevented from scattering toward the support bearing 5 by the airflow generated by the labyrinth seal 11 and fins 10. Since the labyrinth seal 11 and fins 10 are integral, moreover, the fins 10 can be installed in place even though the space between the support bearing 5 and slip ring 1 is narrow.

In an X-ray CT apparatus according to an embodiment shown in FIG. 5, furthermore, labyrinth seals 11 are fixedly installed individually on the opposite side surfaces of a large-diameter circumferential portion 4A so that they are located on either side of a slip ring 1. Also in this case, a small gap is formed between a circumferential end face of a seal ring of each labyrinth seal 11 and the inner peripheral surface of a support frame 3. Since one of the labyrinth seals 11 is disposed so as to close the space between the circumferential portion 4A and the inner peripheral surface of the support frame 3, the slip ring 1 and a support bearing 5 are spatially divided by the one labyrinth seal 11. On the other hand, the slip ring 1 and a space outside the X-ray CT apparatus are spatially divided by the other labyrinth seal 11. Fins 10 are fixedly installed on a side surface of each labyrinth seal 11 nearer to the slip ring 1 so that airflows can be introduced from the space on the side of the support bearing 5 and the space outside the X-ray CT apparatus into a space between the paired labyrinth seals 11 and blown on the slip ring 1. The airflow introduced into the space between the labyrinth seals 11 is directed toward an exhaust port 12, which is formed in a part of the support frame 3 on the stationary side, and is discharged into a dust collection unit 13 through the exhaust port 12 and a duct.

In this embodiment, the pressure in the space between the labyrinth seals 11 is increased by the airflow generated by the fins 10, and the airflow is introduced into the dust collection unit 13 through the exhaust port 12. According to this embodiment, therefore, wear debris is collected in the dust collection unit 13 by the airflow generated by the fins 10. Thus, the wear debris can be prevented from scattering toward the support bearing 5, and the debris collected in the dust collection unit can be easily recovered by means of a dust collector, such as a vacuum cleaner.

Figure 6:
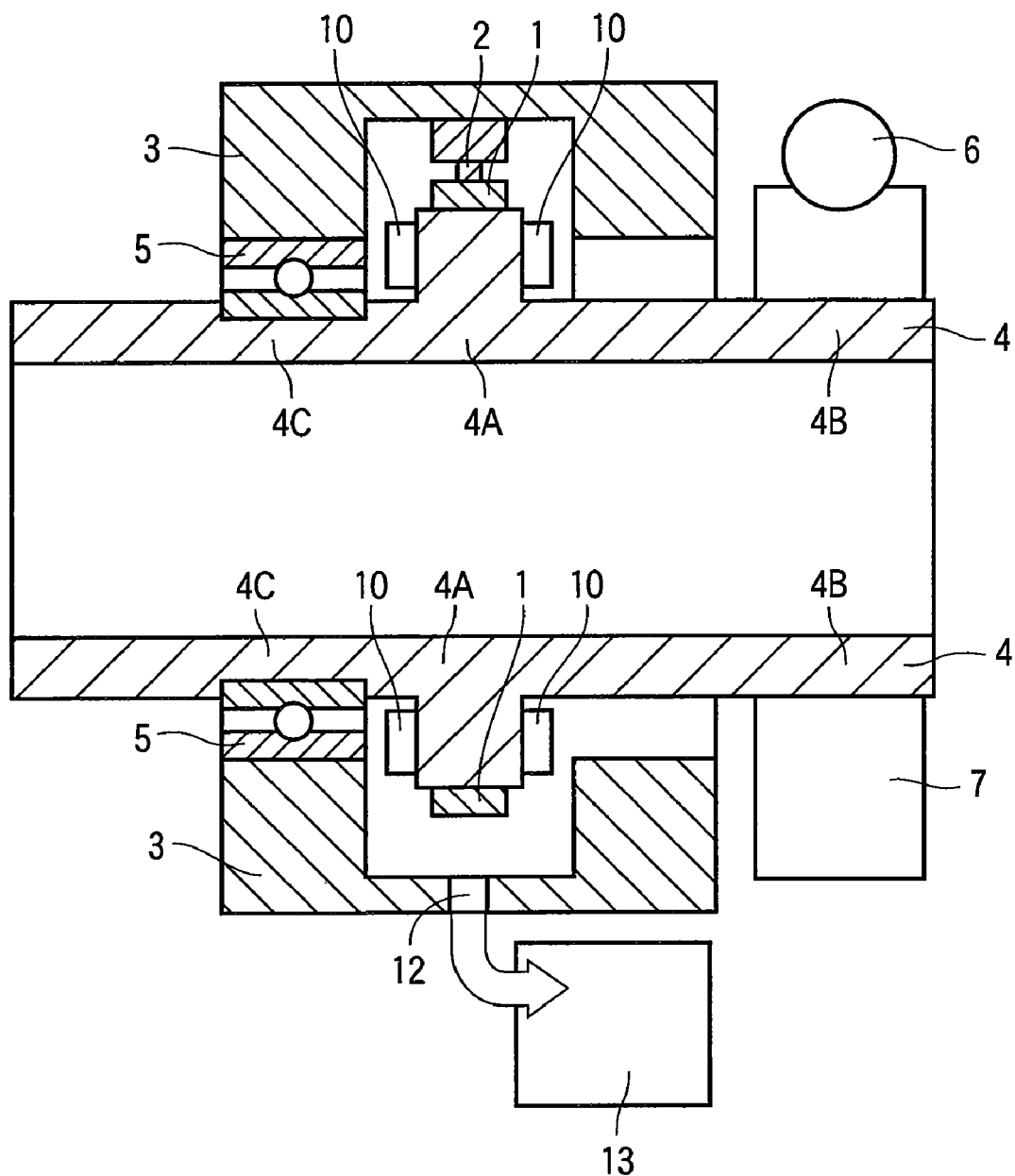
FIG. 6 is a sectional view showing an X-ray CT apparatus according to an additional embodiment of the invention.

In an X-ray CT apparatus according to an embodiment shown in FIG. 6, unlike those shown in FIGS. 1 to 5, an X-ray tube 6 and X-ray detector 7 are disposed on one end portion of a rotating frame 4, a support bearing 5 is disposed on the other side of the rotating frame 4, and a slip ring 1 is located on a large-diameter circumferential portion 4A of the rotating frame 4 between the support bearing 5 and the combination of the X-ray tube 6 and X-ray detector 7. A plurality of fins 10 are fixedly arranged in a rotation direction R on both peripheral surfaces of the circumferential portion 4A of the rotating frame 4. The fins 10 have an airflow orientation which produces airflow directed to a space in which the slip ring 1 is installed from the outside of the apparatus through both the support bearing side and X-ray tube side. Further, an exhaust port 12 is formed in a part of a support frame 3 on the stationary side so as to communicate with the space that accommodates the slip ring 1. This exhaust port is connected to a dust collection unit 13.

Also in this embodiment, wear debris is collected in the dust collection unit 13 by the airflow generated by the fins 10 on the opposite side surfaces of the slip ring 1. Thus, the wear debris can be prevented from scattering toward the support bearing 5 and be recovered with use.

The present invention is not limited directly to the embodiments described above, and in carrying out the invention, its components may be embodied in modified forms without departing from the scope or spirit of the invention. Further, various inventions may be made by suitably combining a plurality of components described in connection with the foregoing embodiments. For example, some of the components according to the foregoing embodiments may be omitted. Furthermore, components according to different embodiments may be combined as required.

The X-ray CT apparatus according to any of the embodiments of the invention described above is characterized in that the fins are arranged in the rotation direction between the slip ring and support bearing on the rotating side. When the fins rotate, airflow is generated that comes out of the X-ray CT apparatus through the space in which the slip ring is installed. Wear debris can be discharged to the outside of the X-ray CT apparatus by this airflow. Thus, the wear debris can be prevented from scattering in the CT apparatus.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography apparatus comprising:
   an X-ray source which irradiates a subject with X-rays;
   an X-ray detection unit which detects the X-rays transmitted through the subject and produces a detection signal;
   a rotating frame which supports the X-ray source and the X-ray detection unit so as to be opposed to each other, said rotating frame is rotated around the subject;
   a bearing which rotatably supports the rotating frame;
   a support frame which supports the bearing;
   an electrically conductive brush which is disposed on the support frame;
   a slip ring which is annularly disposed on the rotating frame in a direction of rotation of the rotating frame, mechanically contacts the brush, and is configured to supply an electrical power to the rotating frame, wear debris being produced in a contact area between the slip ring and the brush;
   a plurality of fins which are arranged between the bearing and the slip ring and are provided on the rotating frame, the plurality of fins are rotated with the rotating frame to produce airflow flowing from a side of the bearing to the outside of the apparatus in such a manner that the airflow transports the wear debris to the outside of the apparatus; and
   a labyrinth seal or a cover plate which is provided between the bearing and the slip ring and is fixed to the rotating frame to prevent the wear debris from being scattered from the contact area.

2. The apparatus according to claim 1, wherein the labyrinth seal or the cover plate has a side surface which is opposed to the slip ring.

3. The apparatus according to claim 1, wherein the labyrinth seal or the cover plate is fixed to the rotating frame and the fins are arranged on the labyrinth seal or the cover plate.

4. An X-ray computed tomography apparatus comprising:
an X-ray source which irradiates a subject with X-rays;
an X-ray detection unit which detects the X-rays transmitted through the subject and produces a detection signal;
a rotating frame which supports the X-ray source and the X-ray detection unit so as to be opposed to each other, said rotating frame is rotated around the subject;
a bearing which supports the rotating frame for rotation;
a support frame which supports the bearing;
an electrically conductive brush which is disposed on the support frame;
a slip ring which is annularly disposed on the rotating frame in a direction of rotation of the rotating frame, mechanically contacts the brush, and is configured to supply an electrical power to the rotating frame, wear debris being produced in a contact area between the slip ring and the brush;
a plurality of fins which is arranged between the bearing and the slip ring and are provided on the rotating frame, the plurality of fins are rotated with the rotating frame to produce airflow flowing from a side of the bearing to the contact space;
an exhaust port which communicates with the contact space through which the airflow is guided and transports the wear debris;
a dust collection unit which is coupled to the exhaust port and serves to collect the wear debris transported through the exhaust port; and
a labyrinth seal or a cover plate which is provided between the bearing and the slip ring and is fixed to the rotating frame to prevent the wear debris from being scattered from the contact area.

5. The apparatus according to claim 4, wherein the labyrinth seal or the cover plate has a side surface which are is opposed to the slip ring.

6. The apparatus according to claim 4, wherein the labyrinth seal or the cover plate is fixed to the rotating frame and the fins are arranged on the labyrinth seal or the cover plate.

7. An X-ray computed tomography apparatus comprising:
an X-ray source which irradiates a subject with X-rays;
an X-ray detection unit which detects the X-rays transmitted through the subject;
a rotating frame which supports the X-ray source and the X-ray detection unit, said rotating frame is rotated around the subject;
a bearing which rotatably supports the rotating frame;
an electrically conductive brush;
a slip ring which is annularly disposed on the rotating frame, wear debris being produced in a contact area between the slip ring and the brush;
a plurality of fins which are arranged on and rotated with the rotating frame; and
a labyrinth seal which is provided between the bearing and the slip ring and is fixed to the rotating frame, wherein the plurality of fins are arranged on the labyrinth seal.

* * * * *